(12) United States Patent
De Cola et al.

(10) Patent No.: US 9,169,434 B2
(45) Date of Patent: Oct. 27, 2015

(54) PHOSPHORESCENT METAL COMPLEX, PROCESS FOR PRODUCTION AND LIGHT-EMITTING COMPONENT

(75) Inventors: Luisa De Cola, Muenster (DE); Claudia Bizzarri, Muenster (DE); David Hartmann, Erlangen (DE); Sabine Szyszkowski, Dachsbach (DE); Wiebke Sarfert, Herzogenaurach (DE); Guenter Schmid, Hemhofen (DE)

(73) Assignee: OSRAM AG, Munich (DE)

( * ) Notice: Subject to any disclaimer, the term of this patent is extended or adjusted under 35 U.S.C. 154(b) by 223 days.

(21) Appl. No.: 13/575,265

(22) PCT Filed: Nov. 17, 2010

(86) PCT No.: PCT/EP2010/067653
§ 371 (c)(1),
(2), (4) Date: Nov. 7, 2012

(87) PCT Pub. No.: WO2011/088916
PCT Pub. Date: Jul. 28, 2011

(65) Prior Publication Data
US 2013/0046096 A1 Feb. 21, 2013

(30) Foreign Application Priority Data
Jan. 25, 2010 (DE) .......................... 10 2010 005 632

(51) Int. Cl.
*C07F 15/00* (2006.01)
*H01L 51/50* (2006.01)
*C09K 11/06* (2006.01)
*H01L 51/00* (2006.01)

(52) U.S. Cl.
CPC ............. *C09K 11/06* (2013.01); *C07F 15/0033* (2013.01); *H01L 51/0067* (2013.01); *H01L 51/0085* (2013.01); *C09K 2211/185* (2013.01); *H01L 51/5032* (2013.01)

(58) Field of Classification Search
USPC .............................................. 546/2; 313/504
See application file for complete search history.

(56) References Cited

U.S. PATENT DOCUMENTS

| 6,830,828 | B2 | 12/2004 | Thompson et al. | |
|---|---|---|---|---|
| 6,902,830 | B2 | 6/2005 | Thompson et al. | |
| 7,001,536 | B2 | 2/2006 | Thompson et al. | |
| 8,062,767 | B2 * | 11/2011 | Cheng et al. ................. | 428/690 |
| 2007/0111025 | A1 | 5/2007 | Lennartz et al. | |

FOREIGN PATENT DOCUMENTS

| DE | 10 2009 031 683 A1 | 3/2011 |
|---|---|---|
| EP | 1 692 244 B1 | 4/2007 |
| EP | 1 904 508 B1 | 8/2009 |
| WO | WO 2005/019373 A2 | 3/2005 |
| WO | WO 2005/097942 A1 | 10/2005 |
| WO | WO 2005/097943 A1 | 10/2005 |
| WO | WO 2006/008976 A1 | 1/2006 |
| WO | WO 2006/013738 A1 | 2/2006 |
| WO | WO 2006/098120 A1 | 9/2006 |
| WO | WO 2007/004113 A2 | 1/2007 |
| WO | WO 2008/000726 A1 | 1/2008 |
| WO | WO 2009/078823 A1 | 6/2009 |
| WO | WO 2011/000616 A1 | 1/2011 |

OTHER PUBLICATIONS

Sambrook, M.R. et al.: Sensitized near infrared emission from lanthanides via anion-templated assembly of d-f heteronuclear [2]pseudorotaxanes. New J. Chem., vol. 30, pp. 1133-1136, 2006.*
Yang C.H., et al., "Blue-Emitting Heteroleptic Iridium(III) Complexes Suitable for High-Efficiency Phosphorescent OLEDs," Angew. Chem. Int. Ed., vol. 46, Feb. 23, 2007, pp. 2418-2421.
Pei, Q., et al., "Polymer Light-Emitting Electrochemical Cells," Science, New Series, vol. 269, No. 5227, Aug. 25, 1995, pp. 1086-1088.
Su, H-C., et al., "Decreased Turn-On Times of Single-Component Light-Emitting Electrochemical Cells by Tethering an Ionic Iridium Complex with Imidazolium Moieties," Chemistry, an Asian Journal, vol. 3, No. 11, XP-002621535, Nov. 13, 2008, pp. 1922-1928.
Vickers, M., et al., "Imidazolium functionalised acyclic ruthenium(II) bipyridyl receptors for anion recognition and luminescent sensing," Journal of Materials Chemistry, vol. 15, XP-002621536, 2005, pp. 2784-2790.

* cited by examiner

*Primary Examiner* — Charanjit Aulakh
(74) *Attorney, Agent, or Firm* — Slater & Matsil, L.L.P.

(57) ABSTRACT

This invention presents, firstly, the principle that simple and known emitter materials which are uncharged per se, as known, for example, from OLED technology, can be converted to a charged species by the introduction of a charged imidazolinium radical. This charged species can then be used in organic light-emitting electrochemical cells.

1 Claim, 3 Drawing Sheets

PHOSPHORESCENT METAL COMPLEX, PROCESS FOR PRODUCTION AND LIGHT-EMITTING COMPONENT

This patent application is a national phase filing under section 371 of PCT/EP2010/067653, filed Nov. 17, 2010, which claims the priority of German patent application 10 2010 005 632.4, filed Jan. 25, 2010, each of which is incorporated herein by reference in its entirety.

TECHNICAL FIELD

The invention relates to a phosphorescent metal complex, to processes for production thereof and to a radiation-emitting component, especially a light-emitting organic electrochemical cell (OLEEC).

BACKGROUND

In contrast to the widely known OLEDs which have already been discussed many times, the latter comprising electron/hole-transporting layers and electron/hole-blocking layers in addition to the emitting layers, a particular feature of the OLEECs is a much simpler construction, since usually only one organic active layer is required here, and this can preferably also be applied via wet-chemical methods in a manner suitable for mass production.

BRIEF DESCRIPTION OF THE DRAWINGS

The more complete understanding of the present invention, and the advantages thereof, reference is now made to the following descriptions taken in conjunction with the accompanying drawing, in which.

DETAILED DESCRIPTION

Figure 1:
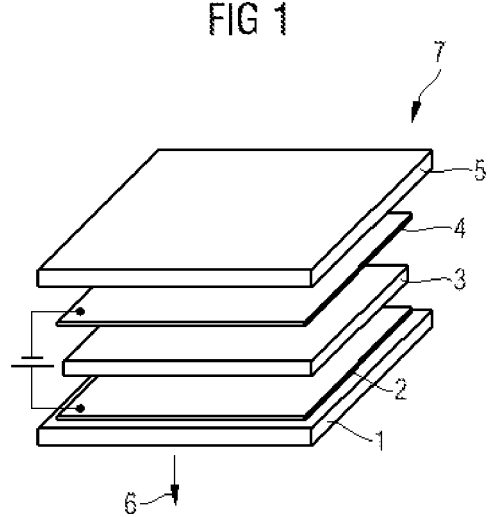
FIG. 1 shows the structure of an OLEEC in schematic form.

In the organic light-emitting diodes (OLEDs), more particularly in the case of the OLEDs formed with what are called small molecules, what is called a multilayer structure is achieved because, in addition to the light-emitting layer, efficiency-enhancing layers such as hole and/or electron injection layers or blocker layers are arranged between the electrodes for better transfer of the charge carriers. Often, high-reactivity materials are used because the materials feature a low work function. Therefore, hermetic encapsulation is essential in the case of OLEDs.

Since the reactive electrodes of the OLED can be dispensed with in the OLEECs, the overall encapsulation problem is not as difficult in the case of the OLEECs as in the case of the OLEDs. The OLEECs are therefore considered to be a promising substitute for the OLEDs.

In quite general terms, organic electroluminescent elements have at least one organic layer present between two electrodes. As soon as voltage is applied to the electrodes, electrons are injected from the cathode into the lowermost unoccupied molecular orbital of the organic light-emitting layer and migrate to the anode.

Correspondingly, holes are injected from the anode into the highest occupied molecular orbital of the organic layer and migrate accordingly to the cathode. In the cases where migrating hole and migrating electron meet a light-emitting substance within the organic light-emitting layer, an exciton forms, which decomposes with emission of light. In order that the light can leave the electroluminescent element at all, at least one electrode has to be transparent; in most cases, one electrode is composed of indium tin oxide, which is used as the anode. The ITO layer is normally deposited on a glass carrier.

There is still an insufficient selection of suitable materials for the emitting layers. More particularly, there is a lack of blue/green-emitting materials.

The solution to the problem and the subject matter of the invention is therefore a charged, cyclometalized metal complex which emits in the visible range under voltage, characterized in that the metal complex has at least one imidazolinium unit bearing a positive charge, bonded via a spacer, on an aromatic structural element of a ligand bonded directly to the central atom.

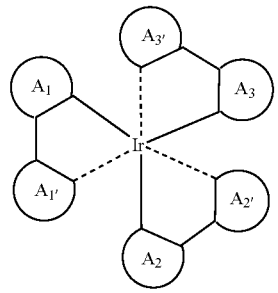

Structural formula I

The structural formula I shows a generalized diagram for the known metal complex emitter materials. Representatively for all emitting systems (see above), iridium complexes with the coordination number of 6 are depicted. Taking account of the coordination number, for example platinum 4, europium usually 8, Os 6, the considerations also apply to other systems. The carbon σ-bond is shown as a solid line, the coordinate bond of the bidentate ligand as a dotted line. The structural formula I shows these conditions in a highly schematic form.

"A" refers in principle to one of the known ligands containing aromatic systems bonded to the central atom, more particularly a substituted or unsubstituted aromatic or heteroaromatic compound capable of the bonding conditions mentioned. All aromatic systems may, like the known structures cited or depicted here, be varied independently of one another. The solid bond to carbon or nitrogen is formed from a C—H or N—H precursor by hydrogen elimination (cyclometalation). The broken line indicates either a carbene carbon or a nitrogen or phosphorus which coordinates through a free electron pair.

According to the invention, an imidazolinium unit is coupled by way of example to at least one of the aromatic systems by means of a spacer.

The spacers used may be:

a) aliphatic chains such as —$(CH_2)_n$— where n=1-20, preferably n=1-5, b) fluorinated alkyl chains having 1-12 carbon atoms in the chain, more preferably 6-10, c) unsaturated alkyl chains having 1-20 carbon atoms and conjugated or nonconjugated double bonds, d) unsaturated alkyl chains having 1-20 carbon atoms and conjugated or nonconjugated triple bonds, also in conjunction with aromatic systems, e) instead of an alkyl chain, it is also possible to use a polyethylene glycol, polyethylenediamine, polyester, polyurethane, polyvinylidenephenylene chain, f) chains containing aromatics; more particularly, it is thus also possible to adjust the geometry of the imidazolinium group compared to the emitter, g) mixed variants of a-f, h) further spacers which are obvious to the person skilled in the art but are not mentioned specially here.

Thus, the overall metal complex receives a charge. What is formed is a metal complex which is represented schematically by the following formulae:

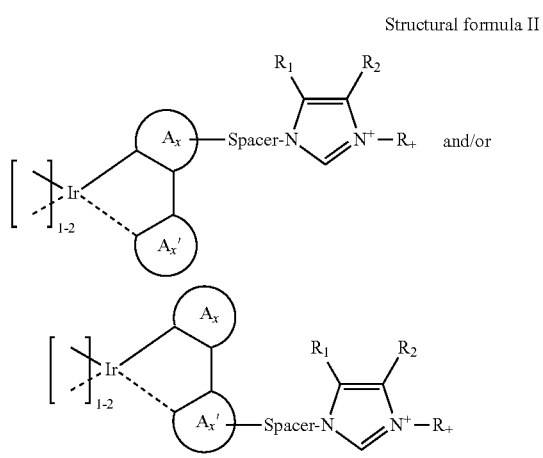

Structural formula II

It is possible to use any other metals, preferably transition metals, for example, but without restriction, Eu, Nd, Gd, Re, Os, Pt, Au, Hg and Ru, Rh, Pd, Ag as well as Ir as the central atom.

The other ligands L may each independently be in a form analogous to the "Ax-spacer-imidazole" ligands imidazolinium-substituted in accordance with the invention, or are selected from the conventional cyclometalizing ligands, as described, for example, in International Patent Publication Nos. WO 2005/097942 A1, WO 2006/013738 A1, WO 2006/098120 A1, WO 2006/008976 A1, WO 2005/097943 A1, (Konica Minolta) or U.S. Pat. No. 6,902,830, U.S. Pat. No. 7,001,536, U.S. Pat. No. 6,830,828 (UDC). They are all bonded to iridium or to the central atom via an N^C unit (example: 2-phenylpyridines or 2-phenylimidazoles and related structures, for example benzimidazoles or phenanthridines).

As already mentioned, the OLEECs in principle need only one active organic layer, which can in principle also be applied by means of methods suitable for mass production, such as simple coating methods, for example spin-coating, knife-coating, dipping, slot die coating, or printing methods such as screen printing, flexographic printing, intaglio printing, inkjet printing.

The typical layer thickness is 10 to 200 nm, but may also assume other values, for example up to 1,000 nm. Since the electrical field in OLEECs declines principally over the electrodes and not over the light-emitting layer, layer thicknesses above 1,000 nm can also still provide good components.

Preferably, for OLEECs, there is no need to use the reactive elements such as barium, calcium, lithium fluoride, cesium fluoride, magnesium etc.; instead, it is possible to use air-stable metals such as gold, palladium, platinum, aluminum, magnesium, silver, copper, nickel, iron, ITO, AZO and alloys thereof.

In the OLEECs, the active layer is a mixture of a conductor for ions and electrons and an emitting species. Ionic transition metal complexes (iTMCs) combine these requirements and are therefore often used in OLEEC applications. A typical representative is ruthenium trisbipyridine hexafluorophosphate $[Ru(bpy)_3]^{2+}(PF_6^-)_2$ described by Q. Pei, G. Yu, C. Zhang, Y. Yang, A. J. Heeger in Science, Vol. 269, 1086-1088, 1995.

When an electrical field is applied to iTMCs, the ions regroup in the electrical field. As a result, a high electrical field is formed at the electrodes, such that both contacts become ohmic contacts, as a result of which charge transfer to the organic layer is facilitated. The charges are then transported through the iTMC layer by "hopping." When holes and electrons meet, they recombine to form excitons, which results in emission of light.

Most of the iTMC materials known to date have ruthenium, osmium, copper or iridium central atoms.

The conventional iridium emitters exhibit at least one phenylpyridine ligand.

Examples of cyclometalized iridium-based emitters are:

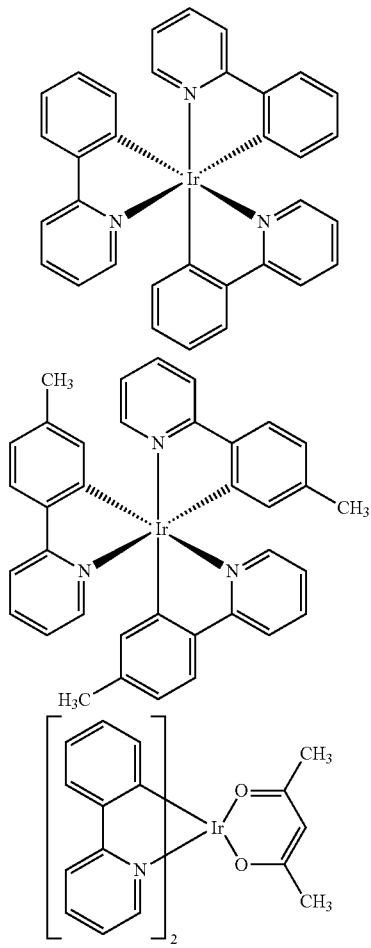

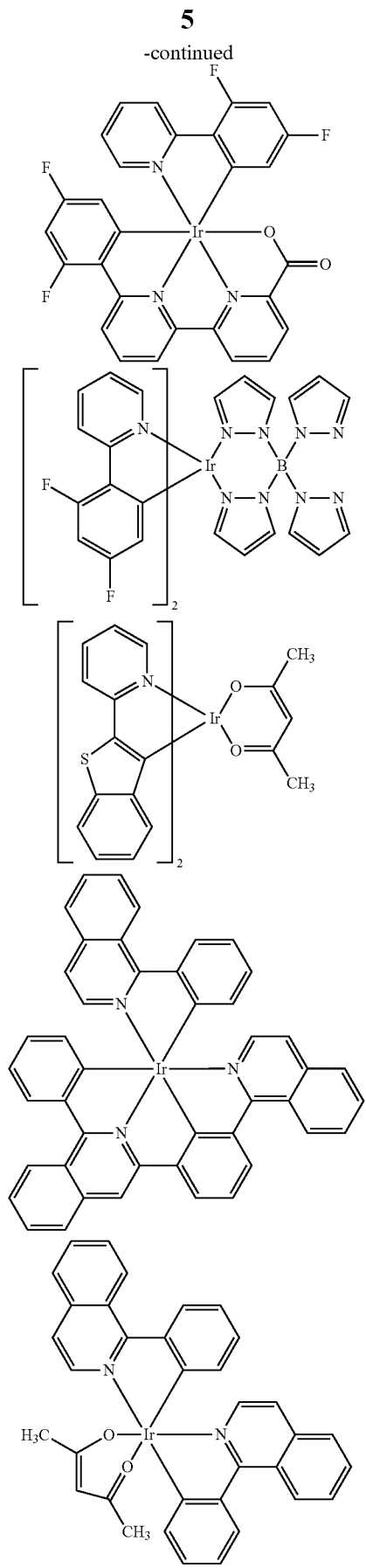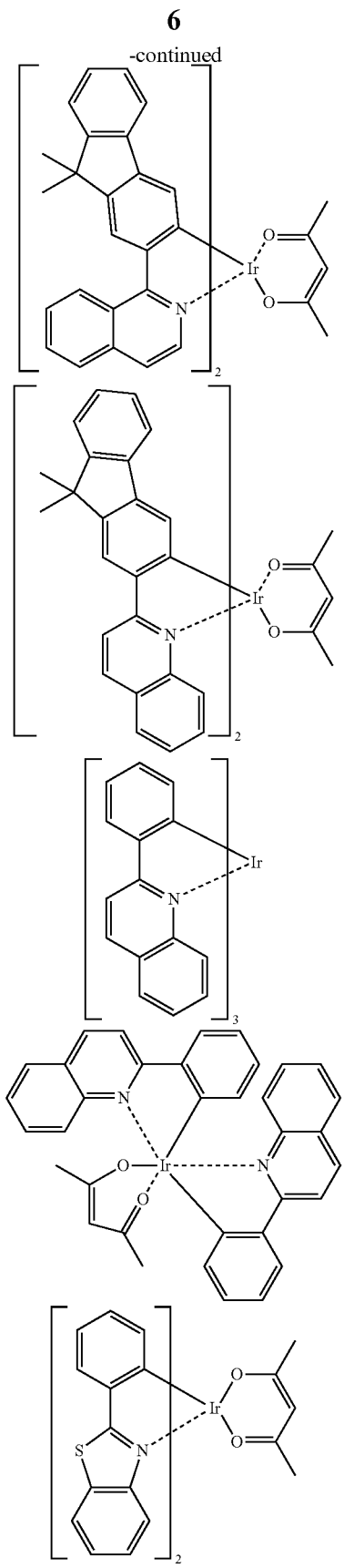
The phenylpyridine ligand is bonded to the central atom in the manner of a cyclometalation to form a direct metal-carbon bond. Some typical iridium complexes with cyclometalation are shown here. Fluorination of the phenylpyridine ligand shifts the emission in the spectrum in the blue direction. Known examples of the fluorinated species are bis(2,4-difluorophenyl-2-pyridyl)iridium(III) picolinate (FIrPic) or bis (2,4-difluorophenylpyridinato)tetrakis(1-pyrazolyl)borate iridium(III) (FIr6).

There are very many emitters for OLED applications, for example typical cyclometalizing ligands as described, for example, in International Patent Publication Nos. WO 2005/097942 A1, WO 2006/013738 A1, WO 2006/098120 A1, WO 2006/008976 A1, WO 2005/097943 A1, (Konica Minolta) or U.S. Pat. No. 6,902,830, U.S. Pat. No. 7,001,536, U.S. Pat. No. 6,830,828 (UDC). All of them are bonded via an NAC unit to iridium or another central atom. Example: 2-phenylpyridine or 2-phenylimidazole and related structures, for example benzimidazole or phenanthridine. Particularly the 2-phenylimidazole derivatives are known for a shift in the emission to the blue-green to blue spectral range.

The known ligands L may, for example, have a further carbene functionality which serves as a source of deep blue emission. Examples of these ligands L can be found in International Patent Publication No. WO 200519373, European Patent Publication No. EP 1692244 B1 or International Patent Publication No. WO 2008/000726 A1.

Further examples of possible ligands L are known from European Patent Publication No. EP 1904508 A2, International Patent Publication No. WO 2007/004113 A2, WO 2007/004113 A3, and these ligands L are also shown in the context of charged metal complexes having at least one phenylpyridine ligand with appropriate donor groups such as dimethylamino. These compounds exhibit an elevated LUMO level of the complex, with introduction of acceptor groups, for example 2,4-difluoro, into the phenyl ring to lower the level of the HOMO orbital. It is shown that the variation of the ligands and substituents thereof can vary the emission color through the entire visible spectrum.

German Patent Publication No. DE 10 2009 031 683 discloses iridium-carbene complexes. In addition, emitting systems are of course not restricted to iridium; instead, it is also possible to form uncharged emitters with lanthanides, especially europium and other heavy metals such as osmium.

Examples of known uncharged emitters:

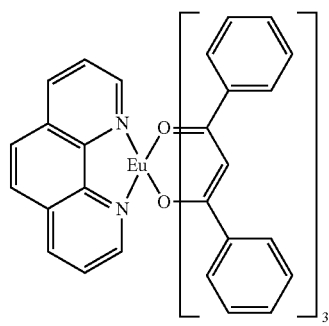

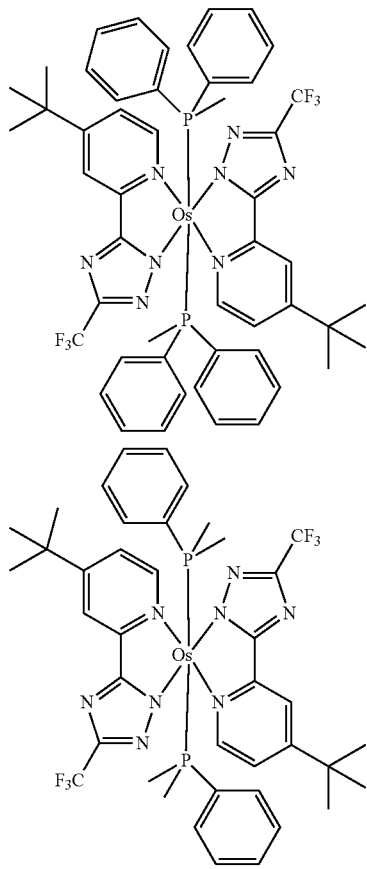

Generally, all radicals are: R=independently H, branched alkyl radicals, unbranched alkyl radicals, fused alkyl radicals, cyclic alkyl radicals, completely or partially substituted unbranched, branched, fused and/or cyclic alkyl radicals, alkoxy groups, amines, amides, esters, carbonates, aromatics, completely or partially substituted aromatics, heteroaromatic compounds, fused aromatics, completely or partially substituted fused aromatics, heterocycles, completely or partially substituted heterocycles, fused heterocycles, halogens, pseudohalogens.

All substituents $R_1$, $R_2$, R+ may each independently be selected from the abovementioned radicals, preferably $C_1$ to $C_{20}$, fused, e.g. decahydronaphthyl, adamantyl, cyclic, cyclohexyl, or fully or partially substituted alkyl radical, preferably $C_1$ to $C_{20}$. These chains or groups may bear various end groups, for example charged end groups such as $SO_x^-$, $NR^+$ and so forth.

The alkyl radicals may in turn bear groups such as ether, ethoxy, methoxy, etc., ester, amide, carbonate, etc., or halogens, preferably fluorine. R, however, shall not be restricted to alkyl radicals, but may instead equally comprise substituted or unsubstituted aromatic systems, for example phenyl, biphenyl, naphthyl, phenanthryl, benzyl, and so forth. A compilation of the most important representatives can be seen in table 1 below.

TABLE 1

| | |
|---|---|
|  Furan |  Thiophene |
| 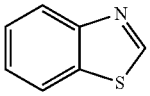 Pyrrole | 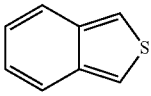 Oxazole |
|  Thiazole |  Imidazole |
| 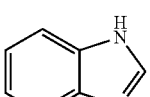 Isoxazole | 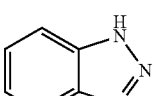 Isothiazole |
|  Pyrazole |  Pyridine |
| 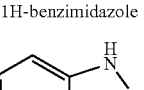 Pyrazine | 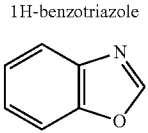 Pyrimidine |
|  1,3,6 Triazine |  Pyrylium |
| 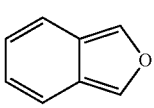 alpha-Pyrone | 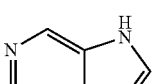 gamma-Pyrone |
|  Benzo[b]furan |  Benzo[b]thiophene |
| 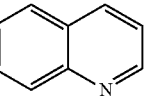 Indole | 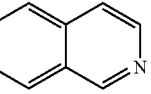 2H-Isoindole |

TABLE 1-continued

| | |
|---|---|
|  Benzothiazole |  2-benzothiophene |
| 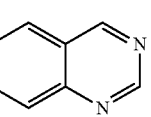 1H-benzimidazole | 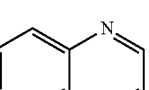 1H-benzotriazole |
|  1H-indazole |  1,3-benzoxazole |
| 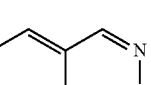 2-benzofuran | 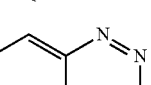 7H-purine |
| 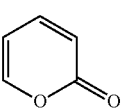 Quinoline |  Isoquinoline |
| 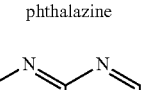 Quinazoline | 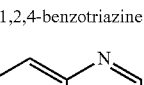 Quinoxaline |
| 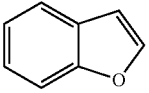 phthalazine | 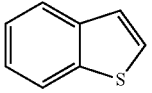 1,2,4-benzotriazine |
| 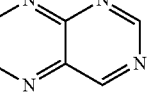 Pyrido[2,3-d]pyrimidine | 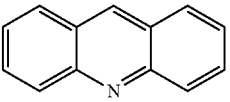 Pyrido[3,2-d]pyrimidine |
| 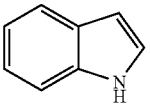 pteridine | 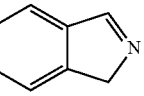 acridine |
| 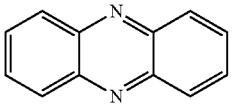 [SMILES: c1ccc2nc3ccccc3nc2c1] phenazine | 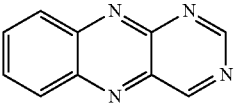 [SMILES: c1ccc2nc3ncncc3nc2c1] benzo[g]pteridine |

TABLE 1-continued

| 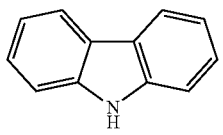 [SMILES: c1ccc2c(c1)[nH]c1ccccc12] | 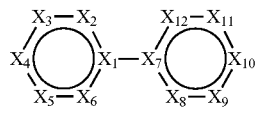 |
|---|---|
| 9H-carbazole | Bipyridine & derivates (0 – 2)(i/ring = N) |

Table 1 shows a selection of substituted and unsubstituted heterocycles which are possible R radicals. For the sake of simplicity, only the base unit is shown. The bond to the ligand may be at any site capable of bonding on the base structure.

R+ introduces the positive charge on the nitrogen atom and is preferably a substituted or unsubstituted aliphatic radical, for example a methyl, ethyl, or a general straight-chain or branched, fused (decahydronaphthyl, adamantyl), cyclic (cyclohexyl) alkyl radical which may be completely or partially substituted and comprises alkyl units having, for example, 1 to 20 carbon atoms.

Preferably, but without restriction, the anions required for compensation of the positive charge are selected from: fluoride, chloride, bromide, iodide, sulfate, phosphate, carbonate, trifluoromethanesulfonate, trifluoroacetate, tosylate, bis(trifluoromethylsulfone)imide, tetraphenylborate, $B_9C_2H_{11}{}^2$; hexafluorophosphate, tetrafluoroborate, hexafluoroantimonate, tetrapyrazolatoborate.

FIG. 1 shows the structure of an OLEEC in schematic form.

An OLEEC 7 is in principle of simpler construction than the OLED and is in most cases realizable by a simple introduction of an organic layer 3 between two electrodes 2 and 4 and subsequent encapsulation 5. On application of voltage, light 6 is emitted. The preferably one active emitting layer 3 of an OLEEC consists of a matrix into which an emitting species has been embedded. The matrix may consist of an insulator or of a material which is either an ion conductor with electrolyte properties or an inert matrix (insulator). The emitting species is/are one or more ionic transition metal complexes (iTMCs for short), for example the compounds according to the present invention, in a polymeric matrix.

On the transparent substrate 1 is the lower electrode layer 2, for example the anode. Above this is the actually active emitting layer 3, and above that the second electrode 4. For better performance and processing, the emitter material (iTMC) which forms the active layer 3, i.e., the phosphorescent metal complex, is dissolved in a solvent together with a matrix material. Preferably, but without restriction, the following solvents are used: acetonitrile, tetrahydrofuran (THF), toluene, ethylene glycol diethyl ether, butoxyethanol, chlorobenzene, propylene glycol methyl ether acetate, further organic and inorganic and polar or nonpolar solvent mixtures are also usable in the context of the invention. The soluble matrix materials which are used in conjunction with iTMCs are, for example, polymers, oligomers and ionic liquids.

The matrix materials used for the construction of an OLEEC according to the invention are preferably ionic liquids which likewise contain an imidazolinium unit. The inventive emitters therefore dissolve very readily in the matrix.

The table below lists some typical representatives of ionic liquids:
1-benzyl-3-methylimidazolium hexafluorophosphate
1-butyl-2,3-dimethylimidazolium hexafluorophosphate
1-butyl-3-methylimidazolium hexafluorophosphate
1-ethyl-3-methylimidazolium hexafluorophosphate
1-hexyl-3-methylimidazolium hexafluorophosphate
1-butyl-1-(3,3,4,4,5,5,6,6,7,7,8,8,8-tridecafluorooctyl)imidazolium hexafluorophosphate
1-methyl-3-(3,3,4,4,5,5,6,6,7,7,8,8,8-tridecafluorooctyl) imidazolium hexafluorophosphate
1-methyl-3-octylimidazolium hexafluorophosphate
1-butyl-2,3-dimethylimidazolium tetrafluoroborate
1-butyl-3-methylimidazolium tetrafluoroborate
1-ethyl-3-methylimidazolium tetrafluoroborate
1-hexyl-3-methylimidazolium tetrafluoroborate
1-methyl-3-octylimidazolium tetrafluoroborate
1-butyl-3-methylimidazolium trifluoromethanesulfonate
1-ethyl-3-methylimidazolium trifluoromethanesulfonate
1,2,3-trimethylimidazolium trifluoromethanesulfonate
1-ethyl-3-methyl-imidazolium bis(pentafluoroethylsulfonyl) imide
1-butyl-3-methylimidazolium bis(trifluoromethylsulfonyl) imide
1-butyl-3-methylimidazolium methanesulfonate
tetrabutylammonium bis-trifluoromethanesulfonimidate
tetrabutylammonium methanesulfonate
tetrabutylammonium nonafluorobutanesulfonate
tetrabutylammonium heptadecafluorooctanesulfonate
tetrahexylammonium tetrafluoroborate
tetrabutylammonium trifluoromethanesulfonate
tetrabutylammonium benzoate
tetrabutylammonium chloride
tetrabutylammonium bromide
1-benzyl-3-methylimidazolium tetrafluoroborate
trihexyltetradecylphosphonium hexafluorophosphate
tetrabutylphosphonium methanesulfonate
tetrabutylphosphonium tetrafluoroborate
tetrabutylphosphonium bromide
1-butyl-3-methylpyridinium bis(trifluoromethylsulfonyl)imide
1-butyl-4-methylpyridinium hexafluorophosphate
1-butyl-4-methylpyridinium tetrafluoroborate sodium tetraphenylborate
tetrabutylammonium tetraphenylborate
sodium tetrakis(1-imidazolyl)borate
cesium tetraphenylborate Examples of polymeric matrix materials (high molecular weight) are, as well as many others: polycarbonate (PC), polymethylmethacrylate (PMMA), polyvinylcarbazole (PVK). As well as these "electrically insulating" materials, it is also possible to use polymeric hole transporters. Typical representatives are: PEDOT (poly(3,4-ethylenedioxythiophene), poly(N,N'-bis(4-butylphenyl)-N,N'-bis(phenyl) benzidine) (PTPD), polyaniline (PANI) and poly(3-hexylthiophene) (P3HT). Any desired copolymers and/or block copolymers of these materials may be used, and these may also contain "insulating" but, for example, solution-mediating units. Examples thereof are polystyrene, ABS, ethylene units, vinyl units etc.

As well as the ionic liquids, it is also possible to use nonionic matrix materials.

Materials with low molecular weight, called small molecules, can likewise be used.

Some examples of hole transporter materials with low molecular weight are listed below:
N,N'-bis(naphthalen-1-yl)-N,N'-bis(phenyl)-9,9-dimethylfluorene
N,N'-bis(3-methylphenyl)-N,N'-bis(phenyl)-9,9-diphenylfluorene
N,N'-bis(naphthalen-1-yl)-N,N'-bis(phenyl)-9,9-diphenylfluorene N,N'-bis(naphthalen-1-yl)-N,N'-bis(phenyl)-2,2-dimethyl-benzidine
N,N'-bis(3-methylphenyl)-N,N'-bis(phenyl)-9,9-spirobifluorene
2,2',7,7'-tetrakis(N,N-diphenylamino)-9,9'-spirobifluorene
N,N'-bis(naphthalen-1-yl)-N,N'-bis(phenyl)benzidine
N,N'-bis(naphthalen-2-yl)-N,N'-bis(phenyl)benzidine
N,N'-bis(3-methylphenyl)-N,N'-bis(phenyl)benzidine
N,N'-bis(3-methylphenyl)-N,N'-bis(phenyl)-9,9-dimethylfluorene
N,N'-bis(naphthalen-1-yl)-N,N'-bis(phenyl)-9,9-spirobifluorene
di[4-(N,N-ditolylamino)phenyl]cyclohexane
2,2',7,7'-tetra(N,N-ditolyl)aminospirobifluorene
9,9-bis[4-(N,N-bis-biphenyl-4-yl-amino)phenyl]-9H-fluorene
2,2',7,7'-tetrakis[N-naphthalenyl(phenyl)amino]-9,9-spirobifluorene
2,7-bis[N,N-bis(9,9-spirobifluorene-2-yl)amino]-9,9-spirobifluorene
2,2'-bis[N,N-bis(biphenyl-4-yl)amino]-9,9-spirobifluorene
N,N'-bis(phenanthren-9-yl)-N,N'-bis(phenyl)benzidine
N,N,N',N'-tetranaphthalen-2-ylbenzidine
2,2'-bis(N,N-diphenylamino)-9,9-spirobifluorene
9,9-bis[4-(N,N-bisnaphthalen-2-ylamino)phenyl]-9H-fluorene
9,9-bis[4-(N,N'-bisnaphthalen-2-yl-N,N'-bisphenylamino)phenyl]-9H-fluorene
titanium oxide phthalocyanine
copper phthalocyanine
2,3,5,6-tetrafluoro-7,7,8,8-tetracyanoquinodimethane
4,4',4"-tris(N-3-methylphenyl-N-phenylamino)triphenylamine
4,4',4"-tris(N-(2-naphthyl)-N-phenylamino)triphenylamine
4,4',4"-tris(N-(1-naphthyl)-N-phenylamino)triphenylamine
4,4',4"-tris(N,N-diphenylamino)triphenylamine
pyrazino[2,3-f][1,10]phenanthroline-2,3-dicarbonitrile
N,N,N',N'-tetrakis(4-methoxyphenyl)benzidine
2,7-bis[N,N-bis(4-methoxyphenyl)amino]-9,9-spirobifluorene
2,2'-bis[N,N-bis(4-methoxyphenyl)amino]-9,9-spirobifluorene
N,N'-di(naphthalen-2-yl)-N,N'-diphenylbenzene-1,4-diamine
N,N'-diphenyl-N,N'-di[4-(N,N-ditolylamino)phenyl]benzidine
N,N'-diphenyl-N,N'-di[4-(N,N-diphenylamino)phenyl]benzidine.

In one embodiment, the following iTMCs are used:

Structure III: Triazole compounds

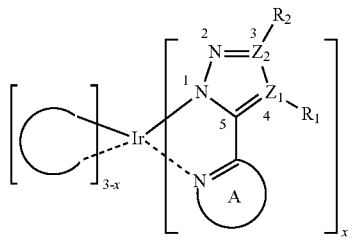

Structure III: Triazole compounds

The emitters described here exhibit, for example, the chemical structure according to structure III with a triazole unit. The invention in this case encompasses both the 1,2,3- and 1,2,4-triazole-based systems. They contain, for example, up to 2 independent "conventional," i.e., already known, ligands, each of which introduces a negative charge into the complex. The third ligand according to the invention may be formed, for example, from a triazole unit with an imidazolinium unit, the nitrogen 1 being bonded to the iridium and having, in position 5 of the triazole ring, a heteroaromatic substituent which forms a coordinate bond from the nitrogen to the iridium.

1,2,3-Triazole compounds are obtained from the structure III through $Z_2$=N and $Z_1$=C, whereas the 1,2,4-triazole compounds form when $Z_2$=C and $Z_1$=N. The ring numbering system has been developed on the basis of the 1,2,3-triazoles and is used in the context of the present invention as shown. When $Z_x$=N, $R_{zx}$ will be absent (x=1 or 2). 1,2,4-Triazoles are obtained by formally exchanging C and N.

$R_{z1}$ for 1,2,3-triazoles ($Z_1$=C, $Z_2$=N) and $R_{z2}$ for 1,2,4-triazoles ($Z_1$=N, $Z_2$=C) on the other hand introduce a charge into the uncharged central iridium complex due to the imidazolinium unit which has been described above.

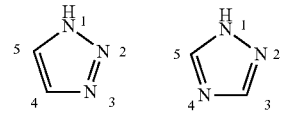

1,2,3-Triazole    1,2,4-Triazole

Some examples are given hereinafter for the ring structure of the heteroaromatic in the ortho position to the two adjacent nitrogens in the triazole ring, for example a 6-membered ring. In the simplest case, this is a pyridine ring or a derivative thereof:

whereas

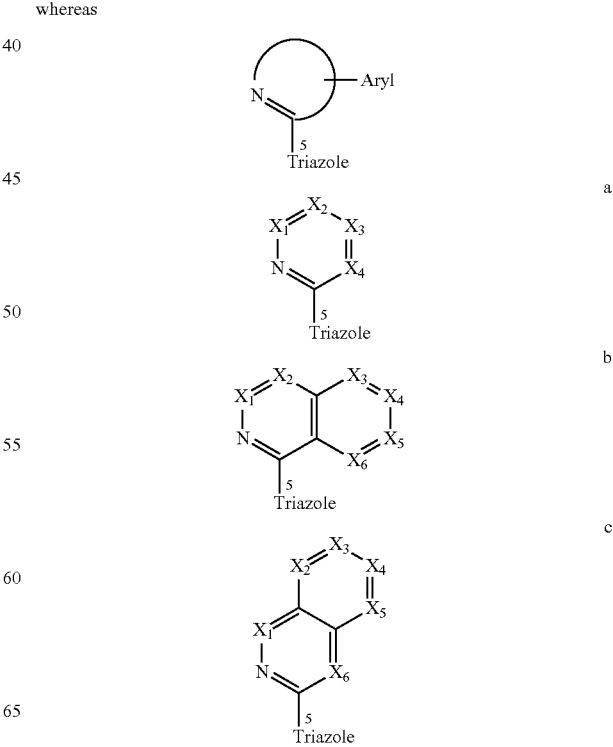

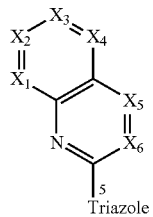

d

Triazole

X is either the —C—R radical where R is one of the substituents below or a nitrogen atom with a free electron pair.

Examples of the substituents "a" on the triazole are:

pyridine derivatives where $X_1$, $X_2$, $X_3$, $X_4$ are all —C—R radicals where all R are independent of one another and are one of the substituents mentioned below.

Pyrimidine derivatives where $X_2$=N or $X_4$=N, all other radicals are —C—R.

Pyrazine derivatives where $X_3$=N, all others are —C—R.

Pyridazine derivatives where $X_1$=N, all others are —C—R.

1,3,5-Triazine derivatives where $X_2$=N and $X_4$=N, all others are —C—R.

Examples of the substituent "b" on the triazole are:

Isoquinoline derivatives where all X are the —C—R radicals with a bond to the triazole ligand in position 1.

Quinazoline derivatives where $X_2$=N, and all other radicals are of the —C—R type.

Phthalazine derivatives where $X_1$=N, and all other radicals are of the —C—R type.

Examples of the substituent "c" on the triazole are:

Isoquinoline derivatives which are structural isomers of the isoquinoline derivatives of the derivatives mentioned above for the substituents "b" on the triazole.

Examples of the substituents "d" on the triazole are:

Quinoline derivatives where all X radicals are of the —C—R type.

Quinoxaline derivatives where $X_5$=N and all others are of the —C—R type.

Quinazoline derivatives where $X_6$=N and all other radicals are of the —C—R type.

More highly fused systems can be prepared analogously, for example pteridine, acridine, phenazine, phenanthridine and/or purine and derivatives thereof, and compounds with additional heteroatoms such as oxygen or sulfur in the fused ring which bears the coordinating nitrogen atom.

Some examples are given hereinafter for the ring structure of the heteroaromatic in the ortho position to the two adjacent nitrogens of the triazole ring, for example a 5-membered ring.

In the simplest case, the 6-membered ring is again a pyridine ring. Examples are given here for five-membered heterosubstituted triazoles:

whereas

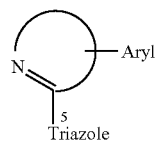

Triazole

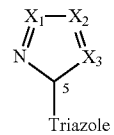

a

Triazole

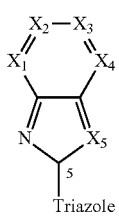

b

Triazole

Examples of the substituent "a" on the triazole are:

Oxazole derivatives where $X_3$=O or $X_2$=O, and all other radicals are of the —C—R type.

Thiazole derivatives where $X_3$=S or $X_2$=S, and all other radicals are of the —C—R type.

Isoxazole derivatives where $X_1$=O and all other radicals are of the —C—R type.

Isothiazole derivatives where $X_1$=S, and all other radicals are of the —C—R type.

Imidazole derivatives where $X_1$, $X_2$ are radicals of the —C—R type and $X_3$ is a radical of the N—R type.

Pyrazole derivatives where $X_2$, $X_3$ radicals of the C—R type and $X_1$ is a radical of the N—R type.

Tetrazole derivatives where $X_1$, $X_2$, $X_3$ are all N.

Examples of the substituent "b" on the triazole are:

Benzimidazole derivatives where $X_5$ is of the N—R type and $X_1$, $X_2$, $X_3$, $X_4$ radicals are of the —C—R type. Further nitrogen atoms may be present in the associated benzene ring, thus forming a benzimidazole-analogous pyridine, pyrimidine, pyrazine or pyridazine ring, by substitution of the C—R for nitrogen.

Examples are purine derivatives: $X_5$ is a radical of the N—R type and $X_1$, $X_3$ are of the N type and $X_4$ is of the —C—R type.

All substituents R may each independently be H, methyl, ethyl, or generally linear or branched, fused (decahydronaphthyl, adamantyl), cyclic (cyclohexyl), or completely or partially substituted alkyl radicals (C1-C20). The alkyl groups may be functional groups such as ether (ethoxy, methoxy, etc.), ester, amide, carbonates etc., or halogens, preferably F. R is not restricted to radicals of the alkyl type, and may instead have substituted or unsubstituted aromatic systems such as phenyl, biphenyl, naphthyl, phenanthryl etc. and benzyl etc. The aromatic systems shown in table 1 can be used again here.

This invention describes phosphorescent ionic emitters for uses in organic light-emitting electrochemical cells. The compounds derive from known OLED emitters, by providing a peripheral substituent of the ligand with an imidazolinium unit.

Advantages:

Stability criteria for OLED emitters can be applied to OLEECs.

Compatibility to the matrix.

Components can be produced by inexpensive wet processes with simultaneous utilization of the advantages of the low molecular weight compounds (easier preparation, reproducibility of the synthesis, good purification options, good solubility).

Specific implementability is demonstrated with triazole compounds.

A specific example of a compound according to the invention is described in detail hereinafter by photochemical and electrical characterization.

The compound

Figure 2:
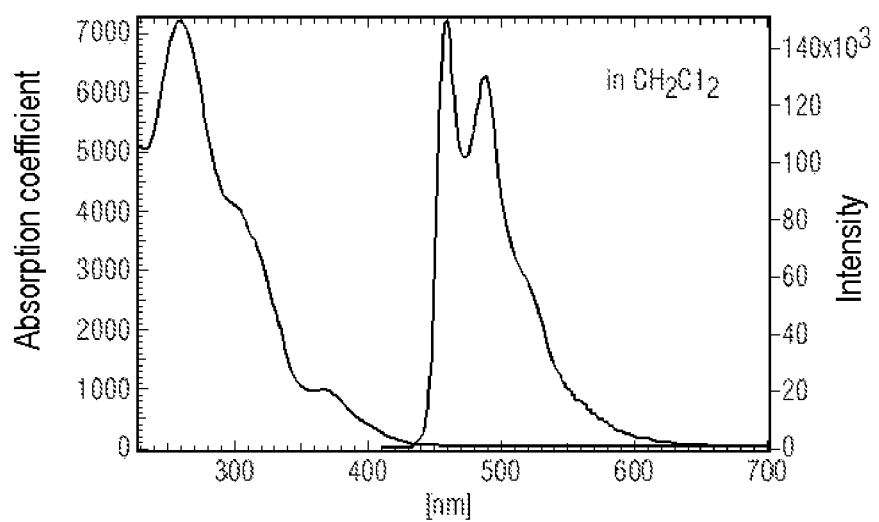
FIG. 2 shows the emission spectrum in $d_1$ chloromethane.

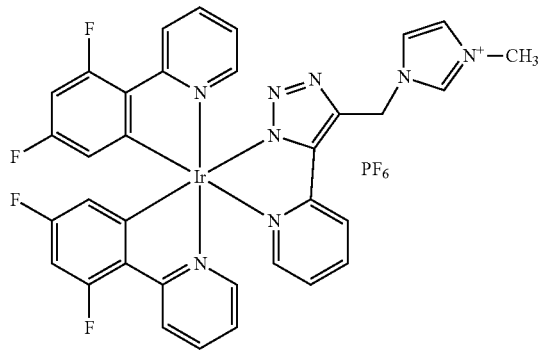

was prepared and studied as follows:

FIG. 2 shows the emission spectrum in dichloromethane, with the maximum emission "excitation" at 368 nm.

Figure 3:
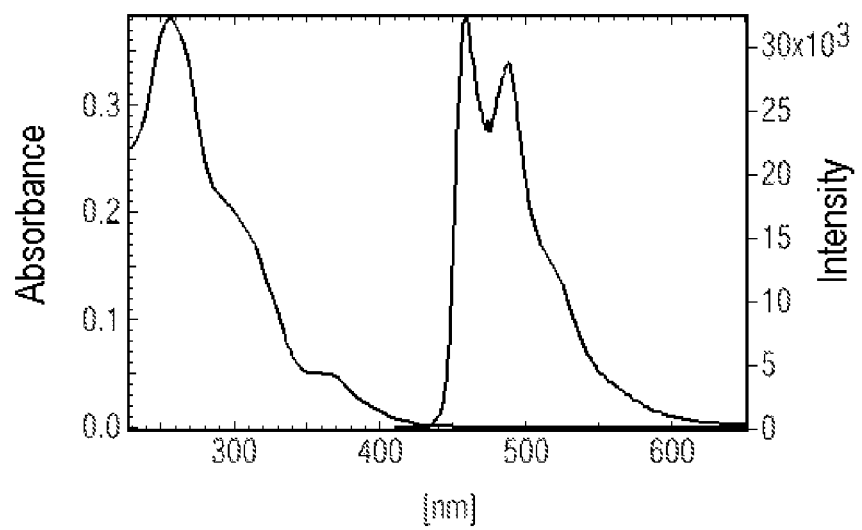
FIG. 3 shows the emission spectrum in air-saturated aceton.

FIG. 3 shows the emission spectrum in air-saturated acetonitrile ("aerated acetonitrile"). The emission spectrum shows a maximum at 355 nm.

Figure 4:
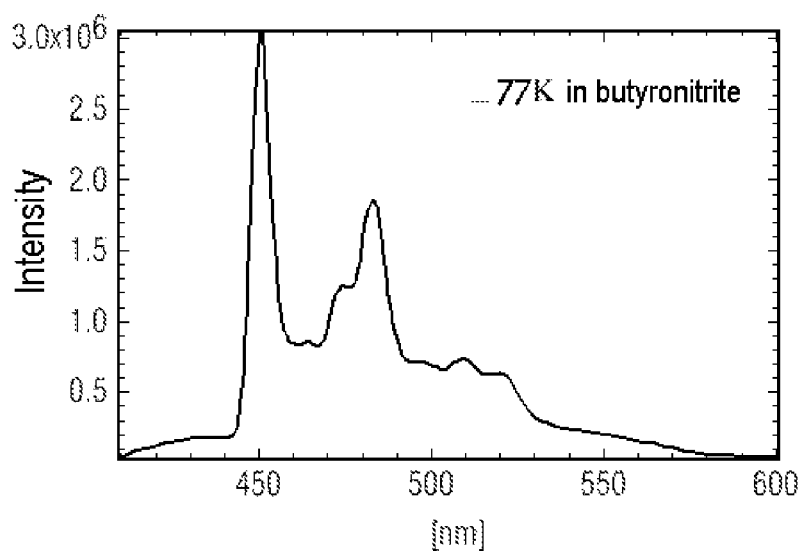
FIG. 4 shows the emission spectrum in buytl nitrate at 77$K_g$.

FIG. 4 shows the emission spectrum in butyl nitrate at 77 K, with emission at 370 nm.

Lifetime Tests:

| λexc | λdetection | τdegas | τaer | τ77K§ |
|---|---|---|---|---|
| 402 nm | 458 nm | 1.15 µs* | 0.26 µs* | 3.76 µs |
|  |  |  | 0.064 µs# |  |

*in DCM
§Measurement wavelength detection at 508 nm, in butyronitrile
in acetonitrile Yield: In air-saturated acetonitrile: ΦAir=0.019 (with quinine as a standard)

In dichloromethane: ΦAir=0.06 (with perylene as a standard) Φdegassed=0.30

Example: (dfppy)$_2$IrTrim PF$_6$ complex tested in the OLEEC component.

The OLEEC component was formed on a prestructured ITO glass substrate. Two layers of the solution were applied by means of spin-coating: 1. A 100 nm Pedot: PSS layer (here: Ai4083 from H. C. Starck) and the emitter solution consisting of (dfppy)$_2$IrTrim PF$_6$+ imidazolinium-PF$_6$ in a molar concentration ratio of 1:1. For the emitter solution, acetonitrile was used as the solvent. As the cathode, an aluminum layer of thickness 200 nm was applied by thermal vapor deposition. The component was sealed by means of an adhesive-bonded glass cap.

Figure 5:
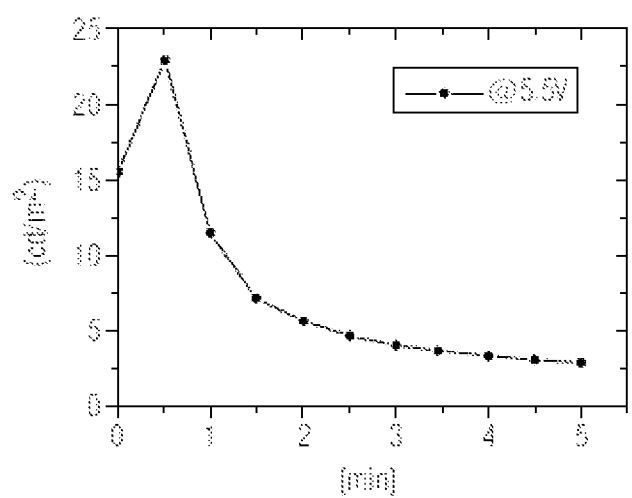
FIG. 5 shows the luminance as a function of time measured at a constant voltage.

FIG. 5 shows the luminance as a function of time measured at a constant voltage of 5.5 V.

According to FIG. 5, the emission extends over virtually the entire visible spectral region, and the light therefore appears white.

This invention presents, firstly, the principle that simple and known emitter materials which are uncharged per se, as known, for example, from OLED technology, can be converted to a charged species by the introduction of a charged imidazolinium radical. This charged species can then be used in organic light-emitting electrochemical cells.

The invention claimed is:

1. A phosphorescent metal complex having the following structure:

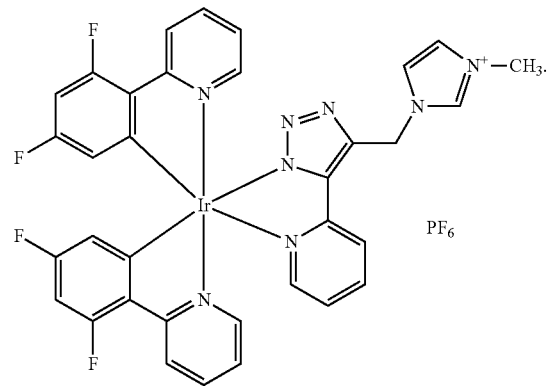

* * * * *